(12) United States Patent
Li et al.

(10) Patent No.: US 10,048,197 B2
(45) Date of Patent: Aug. 14, 2018

(54) OPTICAL MEASUREMENT DEVICE AND OPTICAL MEASUREMENT METHOD

(71) Applicant: Taiwan Biophotonic Corporation, Zhubei (TW)

(72) Inventors: Yu-Tang Li, Zhubei (TW);
Chang-Sheng Chu, Zhubei (TW);
Kuan-Jui Ho, Zhubei (TW);
Pei-Cheng Ho, Zhubei (TW);
Shuang-Chao Chung, Zhubei (TW);
Chih-Hsun Fan, Zhubei (TW);
Jyh-Chern Chen, Zhubei (TW)

(73) Assignee: TAIWAN BIOPHOTONIC CORPORATION, Zhubei (TW)

( * ) Notice: Subject to any disclaimer, the term of this patent is extended or adjusted under 35 U.S.C. 154(b) by 46 days.

(21) Appl. No.: 15/134,405

(22) Filed: Apr. 21, 2016

(65) Prior Publication Data
US 2016/0320298 A1 Nov. 3, 2016

Related U.S. Application Data

(60) Provisional application No. 62/154,083, filed on Apr. 28, 2015.

(51) Int. Cl.
*G01B 9/02* (2006.01)
*G01N 21/45* (2006.01)
(Continued)

(52) U.S. Cl.
CPC ............... *G01N 21/45* (2013.01); *A61B 3/10* (2013.01); *A61B 3/14* (2013.01); *G01N 21/274* (2013.01);
(Continued)

(58) Field of Classification Search
CPC .................. G01N 21/45; G01N 2201/068
(Continued)

(56) References Cited

U.S. PATENT DOCUMENTS

| 4,676,653 A | * | 6/1987 | Strohmeier | .......... | G01N 21/474 |
| | | | | | 356/416 |
| 5,042,951 A | * | 8/1991 | Gold | .................... | G01N 21/211 |
| | | | | | 356/364 |

(Continued)

FOREIGN PATENT DOCUMENTS

| CN | 1227631 A | 9/1999 |
| CN | 102755167 A | 10/2012 |

(Continued)

*Primary Examiner* — Hoa Pham
(74) *Attorney, Agent, or Firm* — Chieh-Mei Wang

(57) ABSTRACT

An optical measurement device includes a light source, first and second beam splitters, and first and second photodetectors. The light source that generates an emitted light beam. The first beam splitter that divides the emitted light beam into a compensation light beam and a measurement light beam. The first beam splitter directs the measurement light beam to a target. The second beam splitter that redirects the compensation light beam from the first beam splitter. A part of wavelength dependent characteristics of the first beam splitter and the second beam splitter are the same. The first photodetector that detects the compensation light beam redirected from the second beam splitter. The second photodetector that detects the measurement light beam reflected by the target and redirected by the first beam splitter. Another optical measurement device and an optical measurement method are also provided.

16 Claims, 18 Drawing Sheets

(51) Int. Cl.
*A61B 3/10* (2006.01)
*A61B 3/14* (2006.01)
*G01N 21/27* (2006.01)
*G01N 21/47* (2006.01)
*G01N 21/55* (2014.01)

(52) U.S. Cl.
CPC ........... *G01N 21/474* (2013.01); *G01N 21/55* (2013.01); *G01N 2201/068* (2013.01)

(58) Field of Classification Search
USPC .................... 356/477, 445, 243.1, 243.8
See application file for complete search history.

(56) References Cited

U.S. PATENT DOCUMENTS

| | | | | |
|---|---|---|---|---|
| 2004/0012770 A1* | 1/2004 | Stierle | ................... | G01B 13/20 |
| | | | | 356/4.01 |
| 2012/0033226 A1* | 2/2012 | Manassen | .............. | G01N 21/55 |
| | | | | 356/477 |
| 2012/0044455 A1* | 2/2012 | Hirose | ............... | G01B 11/2441 |
| | | | | 351/206 |
| 2012/0300217 A1* | 11/2012 | Yuasa | ................... | A61B 3/102 |
| | | | | 356/479 |

FOREIGN PATENT DOCUMENTS

| | | |
|---|---|---|
| CN | 104406544 A | 3/2015 |
| JP | 2013-11589 A | 1/2013 |
| TW | 201229677 A | 7/2012 |

* cited by examiner

OPTICAL MEASUREMENT DEVICE AND OPTICAL MEASUREMENT METHOD

FIELD

The subject matter herein generally relates to an optical measurement device and an optical measurement method.

BACKGROUND

Optical reflective measurement is one of the essential applications of optical analysis. With study of the optical properties of an analyte, people may detect the surface structure, measure the composition of the analyte, or quantify the concentration of a specific compound. The measurement of reflectance provides a remote, contactless, and non-invasive way to extract information from an analyte. Thus, the optical reflective measurement devices are widely used in analytical chemistry, aerospace, and medical fields. A light source, such as laser, is suitable for the applications. However, the instability of the light source and the wavelength dependent characteristics of beam splitter confine precision and accuracy of optical reflective measurement. The instability of the light source includes both the center wavelength drifting and the intensity noise. Also, inhomogeneity of the thin film coating and diffraction of the beam splitter contributes to the non-linear relationship between wavelength and transmittance (or reflectance). The noise resulted from the instability of the light source and the wavelength dependent characteristics of beam splitter hampers the acquisition of fine signals. As a result, the detected signals cannot represent the actual optical power of the reflected light beam.

Current technology has various approaches to improve the performance of such optical devices. First, the stability of the light may be improved by an advanced laser with designs of resonance cavity, laser control circuits, or laser optics, but this approach greatly increase the expense and form factors of the optical reflective measurement device. Second, anti-reflection coating of a beam splitter may mildly reduce diffraction, but still doesn't meet the strict requirement of measurement. Third, people may try to enlarge sample size to increase the statistical power of measurement, but larger sample size needs longer measurement duration or more measurement cycles. Furthermore, non-realtime measurement may not be able to acquire useful signals from many kinds of analytes or under mobile use. For example, some fluidic analyte may be inhomogeneous and flowing, such as vitreous humor in eye or blood in vivo. The present disclosure provides a solution to those technical problems, and the examples are described but not limited to these examples without departing from the scope of disclosure.

BRIEF DESCRIPTION OF THE DRAWINGS

Implementations of the present technology will now be described, by way of example only, with reference to the attached figures.

FIG. 2A shows the power changed over time detected by the first photodetector and the second photodetector. FIG. 2B shows the power detected by the second photodetector normalized by the power detected by the first photodetector.

FIG. 3A shows the reflectance-wavelength characteristic curve and the transmittance-wavelength characteristic curve of a beam splitter, where the reflectance is denoted as R and the transmittance is denoted as T. FIG. 3B shows the power changed over time detected by the first photodetector and the second photodetector. FIG. 3C shows the power detected by the second photodetector normalized by the power detected by the first photodetector.

DETAILED DESCRIPTION

Figure 1:
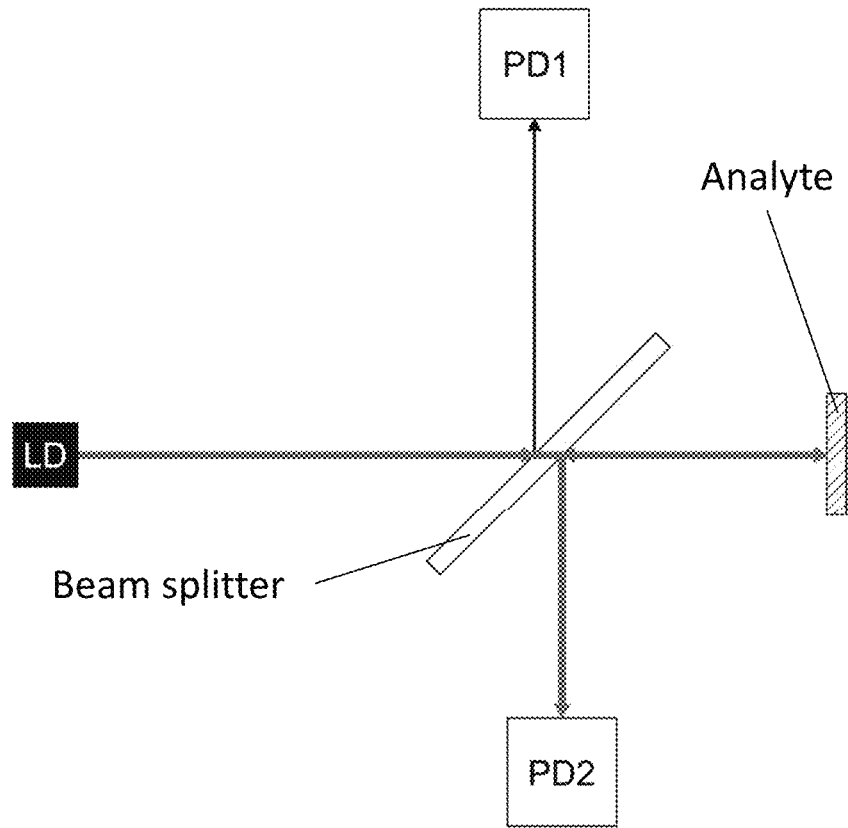
FIG. 1 is a schematic view of conventional configuration of an optical device for reflectance measurement, where the first photodetector is denoted as PD1, the second photodetector is denoted as PD2, and light source is denoted as LD.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "light beam" is defined as a directional projection of light energy, and is not necessarily limited to the optical path directly connected between two optical components. For example, a light beam may come from a light source to a photodetector, with or without passing through a beam splitter between the light source and the photodetector. The direction or the optical properties of a light beam may be changed when passing through an optical component. The term "comprising" means "including, but not necessarily limited to"; it specifically indicates open-ended inclusion or membership in a so-described combination, group, series and the like.

An optical measurement device is configured to measure the reflective light of a target. The target may be a reference mirror or an analyte. The optical measurement device may comprise a reference mirror so that the calibration may be realized by applying the reference mirror as a target. The optical measurement device may be applied on an analyte to measure the optical properties of the analyte by projecting a light beam onto an analyte and measuring the light beam reflected from the analyte. The optical properties may be absorbance, polarization, reflectance, refractive index, fluorescence or inelastic scattering. The principle of an optical measurement device is to project a light beam onto an analyte and to detect the power of reflected light beam as a signal. The analyte may be a mixture of chemical compounds or a part of a biological sample in vivo (for example, blood, skin, eye, or mucosa) or ex vivo (for example, blood, biopsy sample, urine or feces). Furthermore, the analyte may be a reference mirror for calibration of the optical measurement device. The existence or the concentration of a specific biochemical compound in an analyte (for example, glucose, lactate, or hemoglobin) may be estimated by the measured reflectance. In addition, some disease status of an analyte may also be further estimated in vivo or ex vivo, such as keratoconjunctivitis sicca in eye, or dysplasia in a tissue biopsy.

Figure 2A:
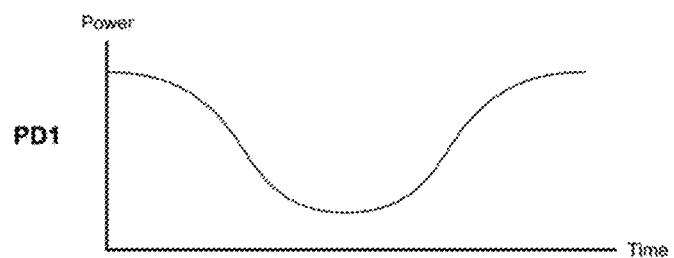
FIGS. 2A-2B show the ideal results of reflectance measurement.
Figure 2A:
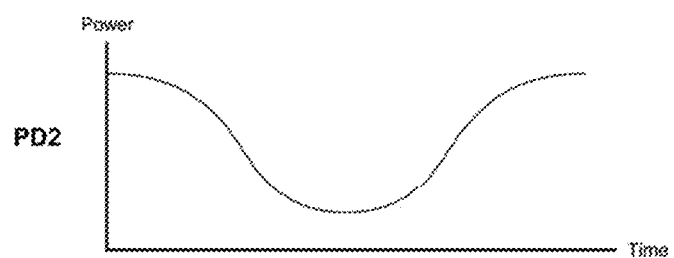
Figure 2B:

As illustrated in FIG. 1, the conventional configuration of an optical measurement device has a photodetector (denoted as PD1) for measurement and the other photodetector (denoted as PD2) for baseline reference. PD1 detects the power of the light beam from the light source, and PD2 detects the power reflected from an analyte. The power detected by PD1 fluctuates over time due to the instability of laser. Ideally, as shown in FIG. 2A, the power detected by PD2 should be consistent with the power detected by PD1, under the assumption of the linearity of the beam splitter between wavelength and reflectance (or transmittance). Thus, the power detected by PD2 can be normalized by the power detected by PD1 as shown in FIG. 2B. It results that the normalized power can infer the reflectance or other optical properties of an analyte.

Figure 3A:
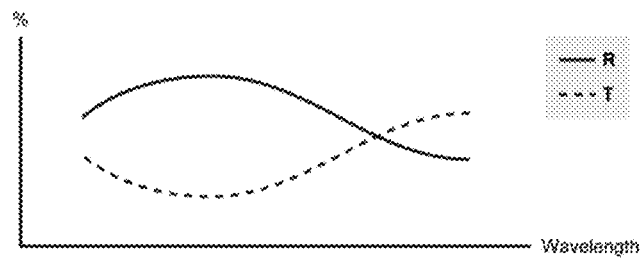
FIGS. 3A-3C show the actual results of reflectance measurement.
Figure 3B:
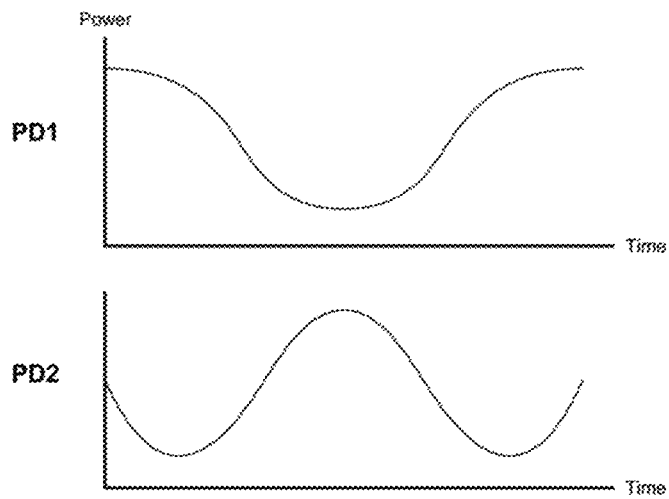
Figure 3C:
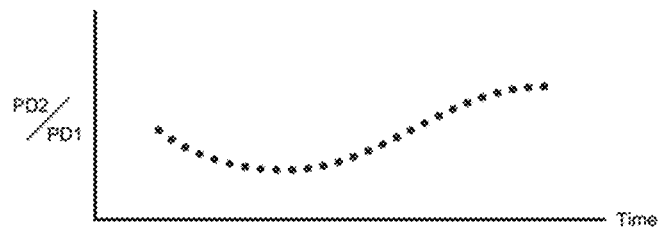

However, the reflectance and the transmittance of a beam splitter changes depending on different wavelengths as the reflectance-wavelength characteristic curve and the transmittance-wavelength characteristic curve shown in FIG. 3A. As shown in FIG. 3B, the power detected by PD2 is not consistent with the power detected by PD1. Therefore, it is not possible to normalize the power detected by PD2 and shows an unpredictable fluctuation as shown in FIG. 3C. In practice, the reflected light is relatively small compared to the power of the light source. As a result, the noise may mask the signal though the noise is a small proportion of the power of the light source. The present disclosure is configured to compensate the noise and accurately measure the reflectance of an analyte.

For clarity of description, the definition of light beam is described according to the directional optical path between the corresponding components. Within the scope of linear optics, a light beam may be decomposed into several light beams by different optical path or by various optical properties; inversely, several light beams may be superposed into a light beam as sharing a common optical path.

An optical measurement device is configured to measure the optical properties of an analyte. The optical measurement device may comprise a light source, a beam splitter, a first photodetector, a second photodetector. An emitted light beam is the light beam emitted by the light source reaching a beam splitter. The emitted light beam is divided by the beam splitter into a compensation light beam and a measurement light beam. A compensation light beam is the light beam directed by the beam splitter to the first photodetector. A measurement light beam is the light beam directed to the analyte by the beam splitter and redirected to the second photodetector by the beam splitter. In the examples, the beam splitter may be a first beam splitter.

The optical measurement device may further comprise a partial reflective mirror. A transmitted part of the measurement light beam is transmitted via the partial reflective mirror, reflected by the analyte, transmitted via the partial reflective mirror and redirected by the beam splitter. A reflected part of the measurement light beam is reflected by the partial reflective mirror, and redirected by the beam splitter. Eventually, the measurement light beam comprising the transmitted part of the measurement light beam and the reflected part of the measurement light beam is detected by the second photodetector.

The optical measurement device may further comprise a third photodetector and a fourth photodetector. In the examples, a first portion of the compensation light beam is detected by the first photodetector and a second portion of the compensation light beam is detected by the third photodetector. A first portion of the measurement light beam is detected by the second photodetector and a second portion of the measurement light beam is detected by the fourth photodetector.

Figure 6A:
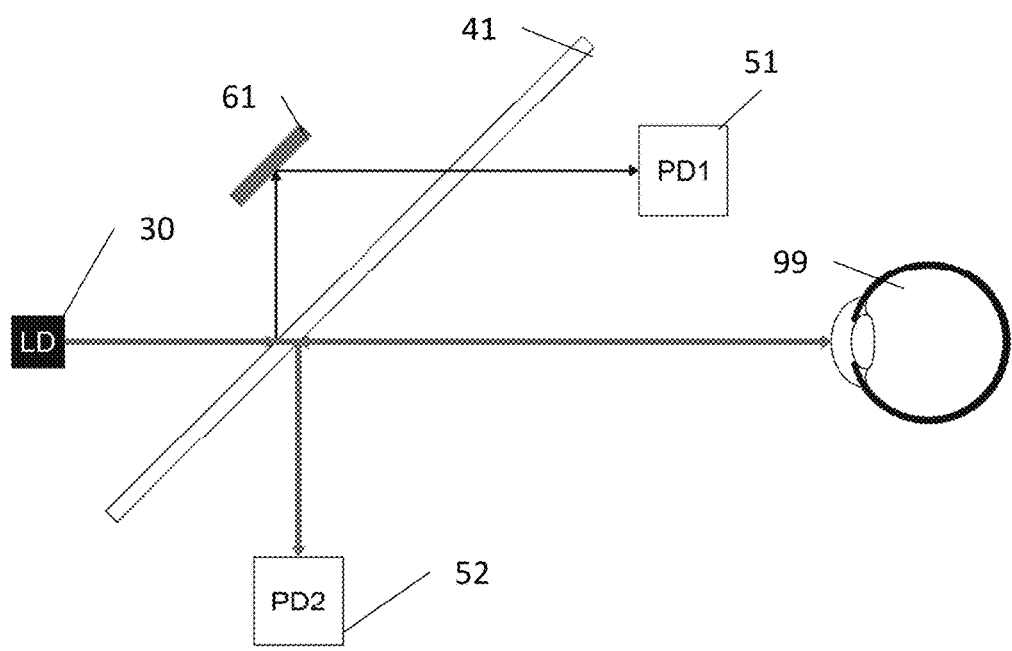
FIG. 6A shows an optical measurement device applied on an analyte.
Figure 6B:
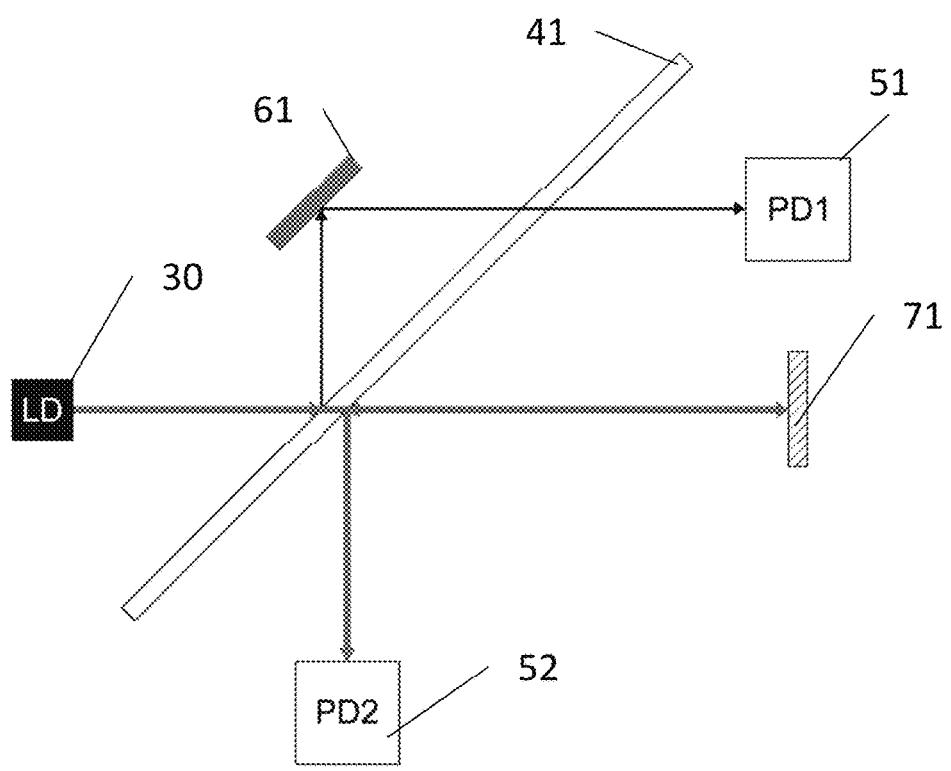
FIG. 6B shows an optical measurement device comprising a reference mirror, and the calibration is confirmed with presence of a reference mirror.

To demonstrate the principle of present disclosure, the examples are illustrated in FIG. 6A and FIG. 6B. The light power of the compensation light beam is detected by the first photodetector 51 and is denoted as $P1=P0*R1*M1*T1$, where P0 represents the total power of emitted light by the light source 30, R1 represents the reflectance of the first beam splitter 41, M1 represents the reflectance of the first mirror 61, and T1 represents the transmittance of the first beam splitter 41. During calibration as shown in FIG. 6B, the analyte is a reference mirror 71. The measurement light beam detected by the second photodetector 52 is denoted as $Pr=P0*T1*Rr*R1$, where Rr represents the reflectance of the reference mirror 71. The normalized power of the measurement light beam during calibration is denoted as $Pc=Pr/P1=Rr/M1$. For Rr and M1 are known constants, Pc is a known constant as well. Therefore, the alignment and calibration can be confirmed. In one example as shown in FIG. 6A, the reference mirror 71 is removed after calibration, and the measurement of an analyte 99 can be implemented with a measurement light beam and a compensation light beam. The power of the measurement light beam is detected by the second photodetector 52 and is denoted as $Pm=P0*T1*F*R1$, where F is the reflectance of an analyte 99. The normalized power of the measurement light beam is denoted as $Pn=Pm/P1=F/M1$. With the constant M1, F can be calculated from Pn. As a result, the noise is compensated by the present disclosure, so that an accurate measurement is achieved. It is contemplated that other examples may be compatible with the present disclosure without departing from the scope of disclosure.

An optical measurement device may comprise a light source, a first beam splitter, a second beam splitter, a first photodetector, and a second photodetector, wherein a part of the wavelength dependent characteristics of the first beam splitter and the second beam splitter are the same. The optical measurement device may further comprise a reference mirror or a partial reflective mirror. It is contemplated that the optical measurement device may further comprise a microprocessor to calculate the normalized power according to the optical power detected by the first photodetector and the second photodetector.

A light source is configured to generate an emitted light beam. A light source may be a coherent light source. At the age of present disclosure, the coherent light source may be a gas laser (for example, helium-neon laser, carbon dioxide laser, carbon monoxide laser, argon-ion lasers, copper vapor laser, or copper bromide vapor laser) a solid state laser (for example, yttrium-aluminum-garnet laser, ruby lasers, or titanium-sapphire laser), or a laser diode. Also, a light source may be a light emitting diode (LED), an organic light emitting diode (OLED), or other non-coherent light sources. A light source may comprise a light emitting element or a composition of multiple light emitting elements. It is contemplated that the light source may further comprise an optical component, such as a bandpass filter, a polarizer, a collimator or the combination, in order to further specify the optical properties of the light source. Within the present disclosure, said light is electromagnetic radiation with the wavelength from ultraviolet, visible light, to infrared regions.

A photodetector is configured to detect the power of a light beam with a specific optical property. The photodetector converts the electromagnetic radiation energy into photocurrent and may be embodied as a photodiode, a phototransistor, a photoresistor, a photomultiplier, or a metal oxide semiconductor (MOS). Also, a photodetector may comprise a linear array or a two dimensional array of charge coupled device (CCD) or complementary metal oxide semiconductor (CMOS). It is contemplated that a photodetector may further comprises amplifiers and/or the analogue to digital converter for the ease of signal processing. A photodetector may further comprise an optical component, such as a bandpass filter or a polarizer, to receive a light beam with specific optical properties.

A beam splitter is capable of splitting a light beam and directing the splitted light beams to two directions. The beam splitter may divide a light beam into two directions according to the optical properties, such as wavelength, polarization, or dividing without biasing the composition of the incident light. For example, a beam splitter may be a polarizing beam splitter, which divides a light beam into two light beams of different polarization. In other examples, a beam splitter may be a dichroic beam splitter, which separates the light beams spectrally. The beam splitter may be configured with different types, such as pellicle type, or polka dot type. Also, the construction of a beam splitter may be embodied as a lens, a plate, or a prism. In general, the transmittance or the reflectance of a beam splitter varies as a function of the wavelength of the incident light, which is referred as the wavelength dependent characteristics. The wavelength dependent characteristics includes the transmittance function and the reflection function. Usually, the sum of the transmittance and the reflectance at any wavelength is approximately one. Preferably, the beam splitters in the optical measurement device have the same wavelength dependent characteristics. It is contemplated that the wavelength dependent characteristics are the same at least in the wavelength range that the wavelength of the emitted light beam drifts around.

In the present disclosure, the beam splitters are also configured to redirect the light beams. A first optical path couples the light source and the first photodetector, and a second optical path couples the light source and the second photodetector. Specifically, the term "redirect" is to balance the light beams in the first optical path and the second optical path.

In the optical measurement device comprising a first beam splitter and a second beam splitter, the amount of transmission by the first beam splitter or the second beam splitter in the first optical path is equal to the amount of transmission by the first beam splitter in the second optical path, and the amount of reflection by the first beam splitter or the second beam splitter in the first optical path is equal to the amount of reflection by the first beam splitter in the second optical path. The second beam splitter may redirect the light beam in the first optical path via transmission or via reflection when the first beam splitter directs the light beam in the first optical path via reflection or via transmission, respectively. For example, the second beam splitter is configured to reflect the compensation light beam when the compensation light beam is transmitted by the first beam splitter, or to transmit the compensation light beam when the compensation light beam is reflected by the first beam splitter.

In the optical measurement device comprising a first beam splitter and a first mirror, the amount of transmission by the first beam splitter in the first optical path is equal to the amount of transmission by the first beam splitter in the second optical path, and the amount of reflection by the first beam splitter in the first optical path is equal to the amount of reflection by the first beam splitter in the second optical path. For example, the first beam splitter is configured to reflect the compensation light beam when the compensation light beam is transmitted by the first beam splitter and reflected by the first mirror, or transmits the compensation light beam when the light beam is reflected by the first beam splitter and reflected by the first mirror.

The optical measurement device may further comprise a third photodetector, a fourth photodetector, a second mirror, and a third mirror. Similarly, a third optical path couples the light source and the third photodetector, and a fourth optical path couples the light source and the fourth photodetector. The amount of transmission by the first beam splitter in the third optical path is equal to the amount of transmission by the first beam splitter in the fourth optical path, and the amount of reflection by the first beam splitter in the third optical path is equal to the amount of reflection by the first beam splitter in the fourth optical path.

A reference mirror is configured to confirm the default calibration before measurement on an analyte. The reference mirror may be configured with a linear relationship between wavelength and reflectance, and or may be configured with a constant reflectance within a certain wavelength of incident light. Therefore, a user may assure that the device is well aligned and the estimation of the reflective measurement is consistent with the known reflectance of the reference mirror. In some examples, the reference mirror may be a partial reflective mirror, which allows partial reflection and partial transmission of an incident light beam on one side and allows transmission from the other side. For example, the partial reflective mirror reflects the reflected part of the measurement light beam, and transmits the transmitted part of the measurement light beam. The optical measurement device comprising the partial reflective mirror is capable of calibration without removal of the partial reflective mirror. Without an analyte placed in front of the partial reflectance mirror, the power of the measurement light beam reflected from outside of the partial reflective mirror reaching the second photodetector may be small enough to be ignored. It is contemplated that a partial reflective mirror may be manufactured from a lens or a glass plate with a partial reflective coating.

An optical measurement device may comprise a light source, a first beam splitter, a second beam splitter, a first photodetector, and a second photodetector. The light source generates an emitted light beam to the first beam splitter. The first beam splitter divides the emitted light beam into a compensation light beam and a measurement light beam. The first beam splitter directs the compensation light beam to the second beam splitter and directs the measurement light beam to an analyte. The second beam splitter redirects the compensation light beam from the first beam splitter to the first photodetector. The first beam splitter redirects the measurement light beam reflected from the analyte to the second photodetector. The first photodetector receives the compensation light beam redirected from the second beam splitter. The second photodetector receives the measurement light beam redirected from the first beam splitter.

Figure 4A:
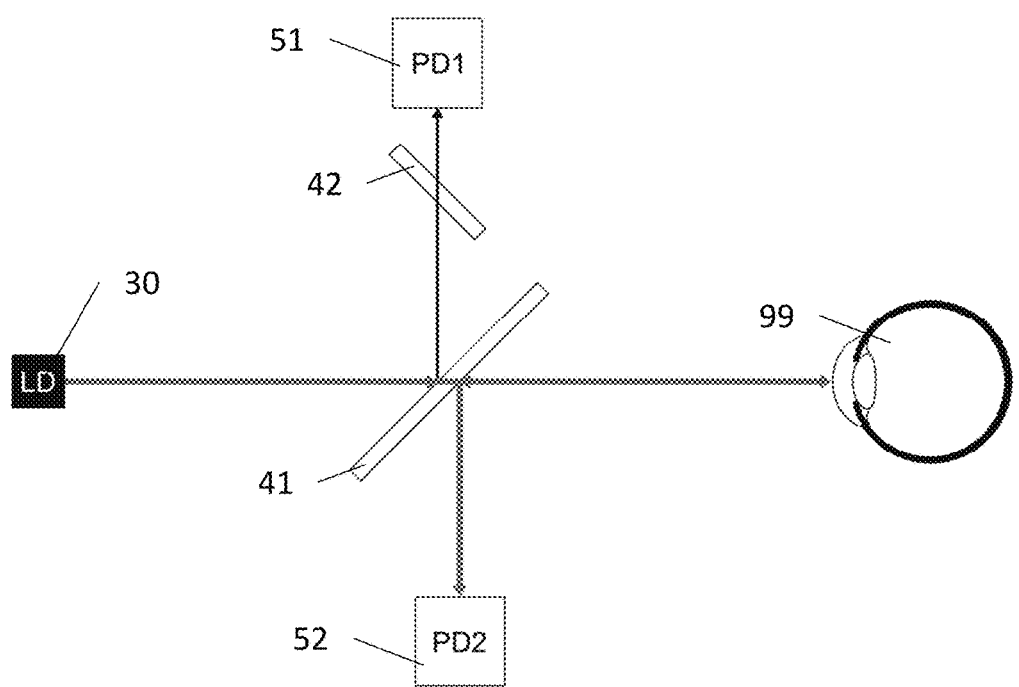
FIG. 4A shows an optical measurement device applied on an analyte.

In one example as illustrated in FIG. 4A, an optical measurement device comprises a light source 30, a first beam splitter 41, a second beam splitter 42, a first photodetector 51, and a second photodetector 52. The light source 30 generates an emitted light beam to the first beam splitter 41. The first beam splitter 41 divides the emitted light beam into a compensation light beam and a measurement light beam. The first beam splitter 41 directs the compensation light beam to the second beam splitter 42 via reflection and directs the measurement light beam to an analyte 99 via transmission. Then, the second beam splitter 42 redirects the compensation light beam to the first photodetector 51 via transmission and the first photodetector 51 detects the compensation light beam. The first beam splitter 41 redirects the measurement light beam reflected by the analyte 99 via reflection and the second photodetector 52 detects the measurement light beam.

Figure 4B:
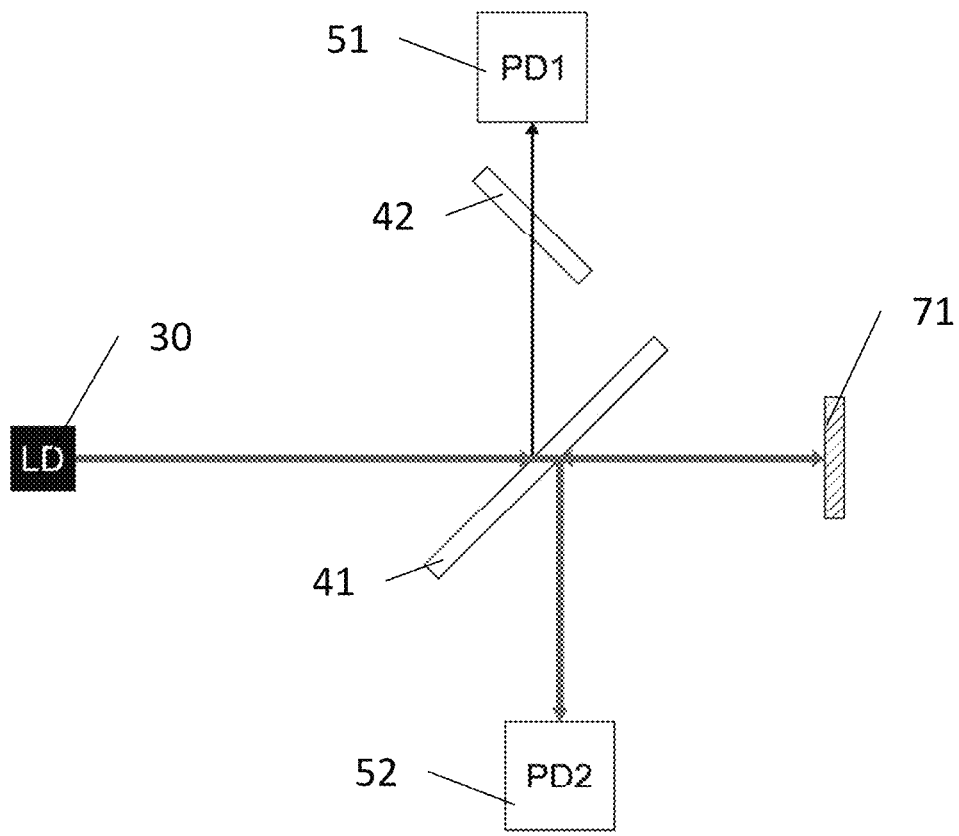
FIG. 4B shows an optical measurement device comprising a reference mirror, and the calibration is confirmed with presence of a reference mirror.

In one example as illustrated in FIG. 4B, an optical measurement device comprises a light source 30, a first beam splitter 41, a second beam splitter 42, a first photodetector 51, a second photodetector 52 and a reference mirror 71. The light source 30 generates an emitted light beam to the first beam splitter 41. The first beam splitter 41 divides the emitted light beam into a compensation light beam and a measurement light beam. The first beam splitter 41 directs the compensation light beam to the second beam splitter 42 via reflection and directs the measurement light beam to the reference mirror 71 via transmission. Then, the second beam splitter 42 redirects the compensation light beam to the first photodetector 51 via transmission and the first photodetector 51 detects the compensation light beam. The first beam splitter 41 redirects the measurement light beam reflected by the reference mirror 71 via reflection. The second photodetector 52 detects the measurement light beam redirected by the first beam splitter 41.

Figure 5A:
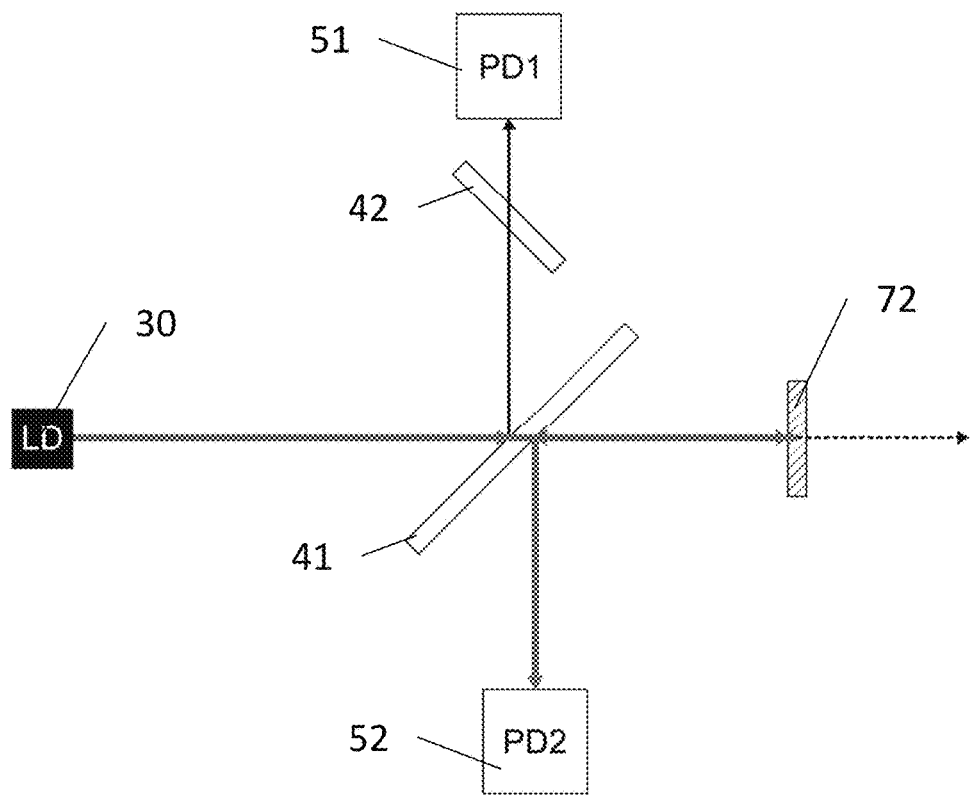
FIG. 5A shows the calibration of an optical measurement device is confirmed with presence of a partial reflective mirror.

In one example as illustrated in FIG. 5A, an optical measurement device comprises a light source 30, a first beam splitter 41, a second beam splitter 42, a first photodetector 51, a second photodetector 52 and a partial reflective mirror 72. The light source 30 generates an emitted light beam to the first beam splitter 41. The first beam splitter 41 divides the emitted light beam into a compensation light beam and a measurement light beam. The first beam splitter 41 directs the compensation light beam to the second beam splitter 42 via reflection and directs the measurement light beam to the partial reflective mirror 72 via transmission. The second beam splitter 42 redirects the compensation light beam to the first photodetector 51 via transmission. The first photodetector 51 detects the compensation light beam redirected by the second beam splitter 42. The partial reflective mirror 72 reflects the reflected part of the measurement light beam to the first beam splitter 41 and transmits the transmitted part of the measurement light beam to the outside of the partial reflective mirror 72. The first beam splitter 41 redirects the reflected part of the measurement light beam via reflection. The second photodetector 52 detects the measurement light beam redirected by the first beam splitter 41. The power of the transmitted part of the measurement light beam reflected by an analyte can be ignored during calibration.

Figure 5B:
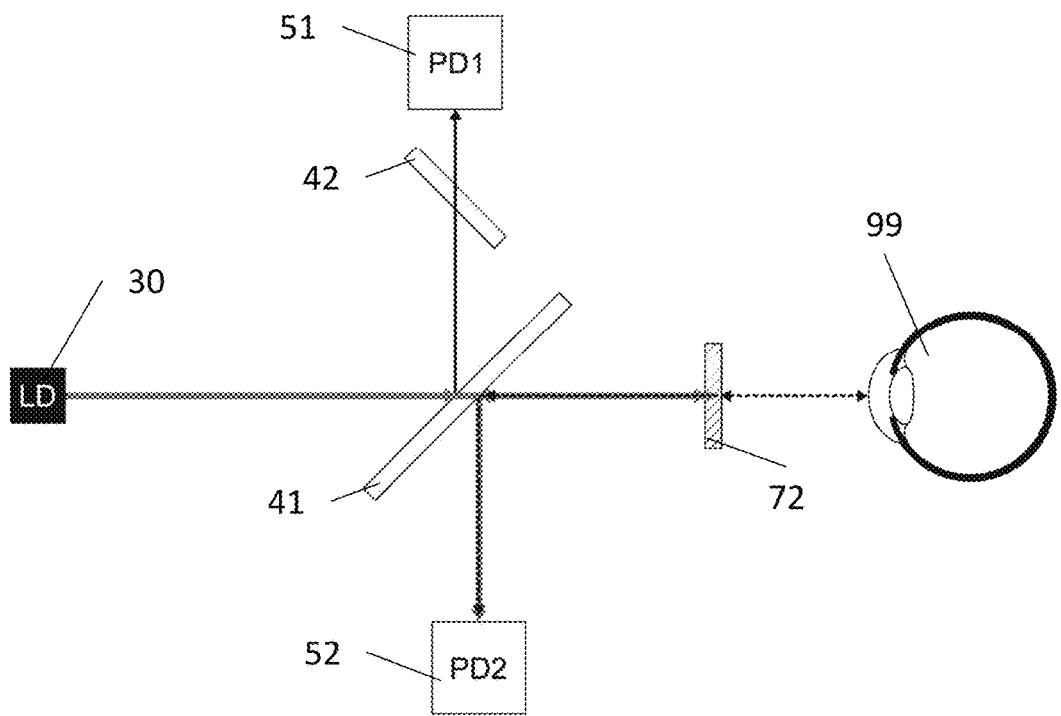
FIG. 5B shows an optical measurement device comprising a partial reflective mirror applied on an analyte.

As illustrated in FIG. 5B, the optical measurement device is applied on an analyte 99. With the analyte 99 in front of the partial reflective mirror 72, the measurement light beam is reflected by the analyte 99 back to the first beam splitter 41 and detected by the second photodetector 52. The light source 30 generates an emitted light beam to the first beam splitter 41. The first beam splitter 41 divides the emitted light beam into a compensation light beam and a measurement light beam. The first beam splitter 41 directs the compensation light beam to the second beam splitter 42 via reflection and directs the measurement light beam to the partial reflective mirror 72 via transmission. The second beam splitter 42 redirects the compensation light beam to the first photodetector 51 via transmission. The first photodetector 51 detects the compensation light beam redirected by the second beam splitter 42. The partial reflective mirror 72 reflects the reflected part of the measurement light beam to the first beam splitter 41 and transmits the transmitted part of the measurement light beam to an analyte 99. The first beam splitter 41 redirects the measurement light beam comprising the reflected part of the measurement light beam reflected by the partial reflective mirror 72 via reflection and the transmitted part of the measurement light beam reflected by the analyte 99. The second photodetector 52 detects the measurement light beam redirected by the first beam splitter 41.

An optical measurement device may comprise a light source, a first beam splitter, a first photodetector, a second photodetector, and a first mirror. A mirror is configured to reflect incident light in some range of wavelengths (for example, ultraviolet, visible, near infrared or far infrared regions), and the reflected light preserves many or most of the optical properties of the incident light, such as wavelength, polarization, or intensity. A mirror may be embodied as a plate of solid metal (for example, bronze or silver), or may be embodied as a plate with coatings (for example, silver, aluminum, gold, or dielectric coatings). In the examples of the present disclosure, an optical measurement device may have multiple mirrors, and these mirror may have same linear relationship between wavelength and reflectance, or each may have different measurable reflectance in some range of wavelengths.

In one example as illustrated in FIG. 6A, an optical measurement device comprises a light source 30, a first beam splitter 41, a first photodetector 51, a second photodetector 52, and a first mirror 61. The light source 30 generates an emitted light beam to the first beam splitter 41. The first beam splitter 41 divides the emitted light beam into a compensation light beam and a measurement light beam. The first beam splitter 41 directs the compensation light beam to the first mirror 61 via reflection and directs the measurement light beam to an analyte 99 via transmission. The first mirror 61 reflects the compensation light beam to the first beam splitter 41. The first beam splitter 41 redirects the compensation light beam to the first photodetector 51 via transmission. The first photodetector 51 detects the compensation light beam redirected by the first beam splitter 41. The first beam splitter 41 redirects the measurement light beam reflected by the analyte 99. The second photodetector 52 detects the measurement light beam redirected by the first beam splitter 41.

In one example as illustrated in FIG. 6B, an optical measurement device comprises a light source 30, a first beam splitter 41, a first photodetector 51, a second photodetector 52, a first mirror 61 and a reference mirror 71. The reference mirror 71 may be removed after the confirmation of calibration. The light source 30 generates an emitted light beam to the first beam splitter 41. The first beam splitter 41 divides the emitted light beam into a compensation light beam and a measurement light beam. The first beam splitter 41 directs the compensation light beam to the first mirror 61 via reflection and directs the measurement light beam to the reference mirror 71 via transmission. The first mirror 61 reflects the compensation light beam to the first beam splitter 41. The first beam splitter 41 redirects the compensation light beam to the first photodetector 51 via transmission. The first photodetector 51 detects the compensation light beam redirected by the first beam splitter 41. The first beam splitter 41 redirects the measurement light beam reflected by the reference mirror 71 via reflection. The second photodetector 52 detects the measurement light beam redirected by the first beam splitter 41. It is contemplated that the optical measurement device may further comprise a second mirror reflecting the measurement light beam from the first beam splitter 41 to the second photodetector 52 to balance the wavelength-dependent characteristics between the first mirror and the second mirror, or to adjust the length of the first optical path matching the second optical path.

Figure 7A:
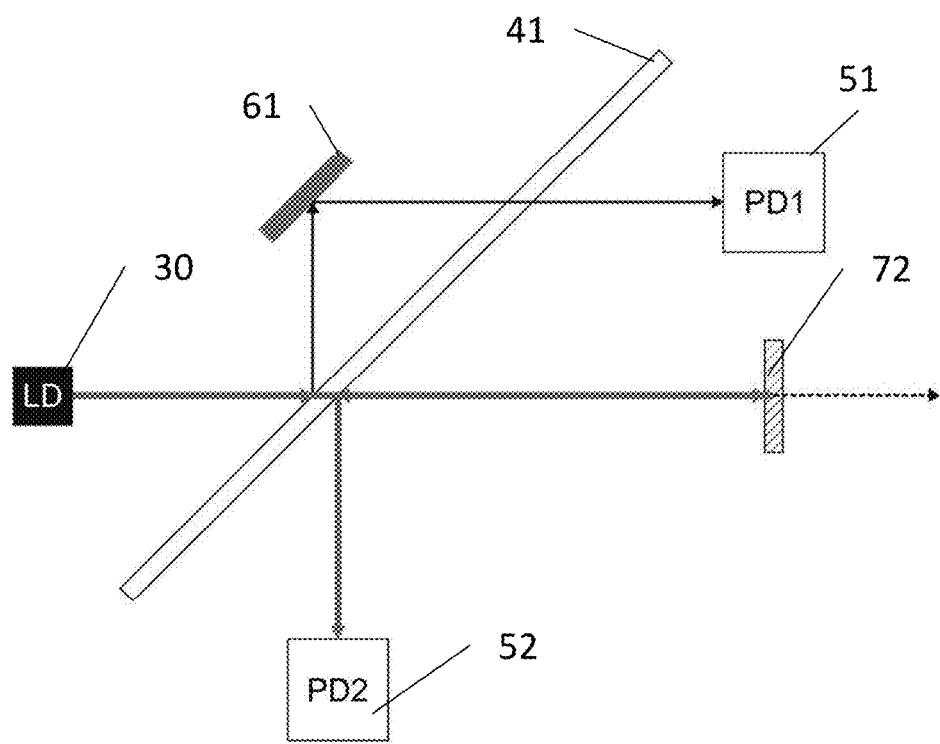
FIG. 7A shows the calibration of an optical measurement device is confirmed with presence of a partial reflective mirror.

In one example as illustrated in FIG. 7A, an optical measurement device comprises a light source 30, a first beam splitter 41, a first photodetector 51, a second photodetector 52, a first mirror 61 and a partial reflective mirror 72. The light source 30 generates an emitted light beam to the first beam splitter 41. The first beam splitter 41 divides the emitted light beam into a compensation light beam and a measurement light beam. The first beam splitter 41 directs the compensation light beam to the first mirror 61 via reflection and directs the measurement light beam to the partial reflective mirror 72 via transmission. The first mirror 61 reflects the compensation light beam to the first beam splitter 41. The first beam splitter 41 redirects the compensation light beam to the first photodetector 51 via transmission. The first photodetector 51 detects the compensation light beam redirected by the first beam splitter 41. The partial reflective mirror 72 reflects the reflected part of the measurement light beam to the first beam splitter 41 and transmits and the transmitted part of the measurement light beam to the outside of the partial reflective mirror 72. The first beam splitter 41 redirects the reflected part of the measurement light beam reflected by the partial reflective mirror 72 via reflection. The second photodetector 52 detects the measurement light beam redirected by the first beam splitter 41.

Figure 7B:
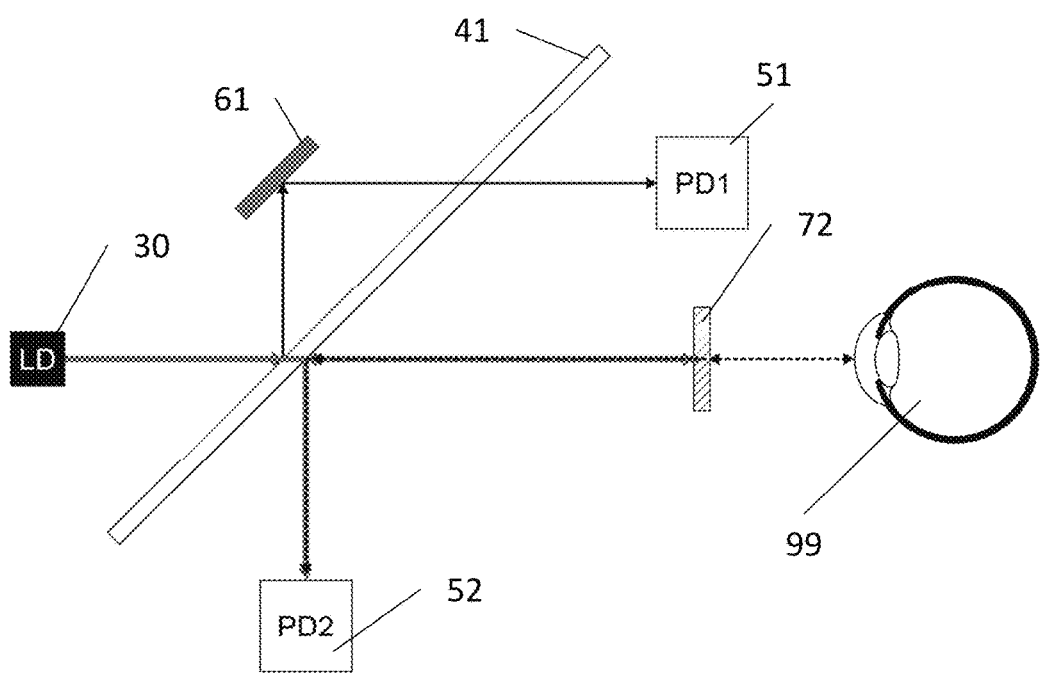
FIG. 7B shows an optical measurement device comprising a partial reflective mirror applied on an analyte.

In one example as illustrated in FIG. 7B, the optical measurement device is applied on an analyte 99. With the analyte 99 in front of the partial reflective mirror 72, the measurement light beam is reflected by the analyte 99 back to the first beam splitter 41 and detected by the second photodetector 52. The light source 30 generates an emitted light beam to the first beam splitter 41. The first beam splitter 41 divides the emitted light beam into a compensation light beam and a light beam comprising a measurement light beam. The first beam splitter 41 directs the compensation light beam to the first mirror 61 via reflection and directs the measurement light beam to the partial reflective mirror 72 via transmission. The first mirror 61 reflects the compensation light beam to the first beam splitter 41. The first beam splitter 41 redirects the compensation light beam to the first photodetector 51 via transmission. The first photodetector 51 detects the compensation light beam redirected by the first beam splitter 41. The partial reflective mirror 72 reflects the reflected part of the measurement light beam to the first beam splitter 41 and transmits the transmitted part of the measurement light beam to an analyte 99. The first beam splitter 41 redirects the measurement light beam comprising the reflected part of the measurement light beam reflected by the partial reflective mirror 72 via reflection and the transmitted part of the measurement light beam reflected by the analyte. The second photodetector 52 detects the measurement light beam redirected by the first beam splitter 41.

In order to measure two different optical properties, an optical measurement device may have two photodetectors for measurement and each has a corresponding photodetector to compensate the noise.

Figure 8A:
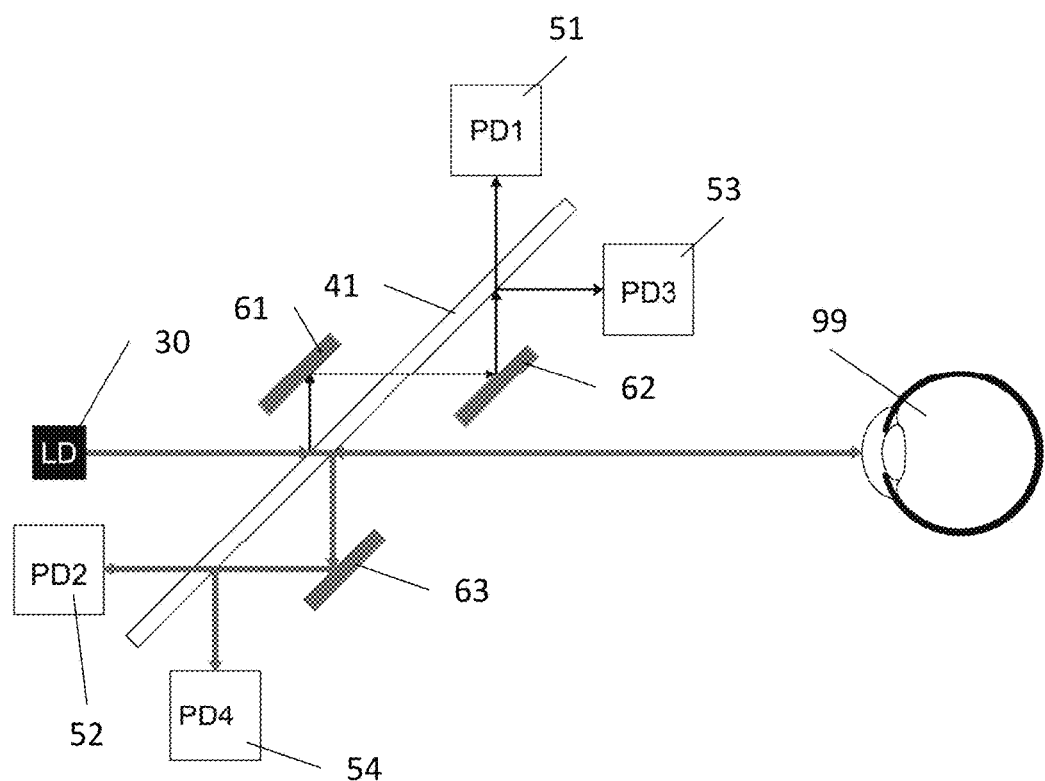
FIG. 8A shows an optical measurement device comprising two pairs of photodetectors applied on an analyte.

In one example as illustrated in FIG. 8A, an optical measurement device comprises a light source 30, a first beam splitter 41, a first photodetector 51, a second photodetector 52, a third photodetector 53, a fourth photodetector 54, a first mirror 61, a second mirror 62, and a third mirror 63. The light source 30 generates an emitted light beam to the first beam splitter 41. The first beam splitter 41 divides the emitted light beam into a compensation light beam and a measurement light beam. The first beam splitter 41 directs the compensation light beam to the first mirror 61 via reflection and directs the measurement light beam to an analyte 99 via transmission. The first mirror 61 reflects the compensation light beam to the first beam splitter 41. The first beam splitter 41 redirects the compensation light beam to the second mirror 62 via transmission. The second mirror 62 reflects the compensation light beam from the first beam splitter 41 back to the first beam splitter 41. The first beam splitter 41 divides the compensation light beam into a first portion of the compensation light beam and a second portion of the compensation light beam. The first beam splitter 41 redirects the first portion of the compensation light beam to the first photodetector 51 via transmission and redirects the second portion of the compensation light beam to the third photodetector 53 via reflection. The first photodetector 51 detects the first portion of the compensation light beam redirected by the first beam splitter 41 and the third photodetector 53 detects the second portion of the compensation light beam redirected by the first beam splitter 41. The first beam splitter 41 redirects the measurement light beam reflected by the analyte 99. The third mirror 63 reflects the measurement light beam from the first beam splitter 41 back to the first beam splitter 41. The first beam splitter 41 divides the measurement light beam into a first portion of the measurement light beam and a second portion of the measurement light beam. The first beam splitter 41 redirects the first portion of the measurement light beam to the second photodetector 52 via transmission and redirects the second portion of the measurement light beam to the fourth photodetector 54 via reflection. The second photodetector 52 detects the first portion of the measurement light beam redirected by the first beam splitter 41 and the fourth photodetector 54 detects the second portion of the measurement light beam redirected by the first beam splitter 41.

Figure 8B:
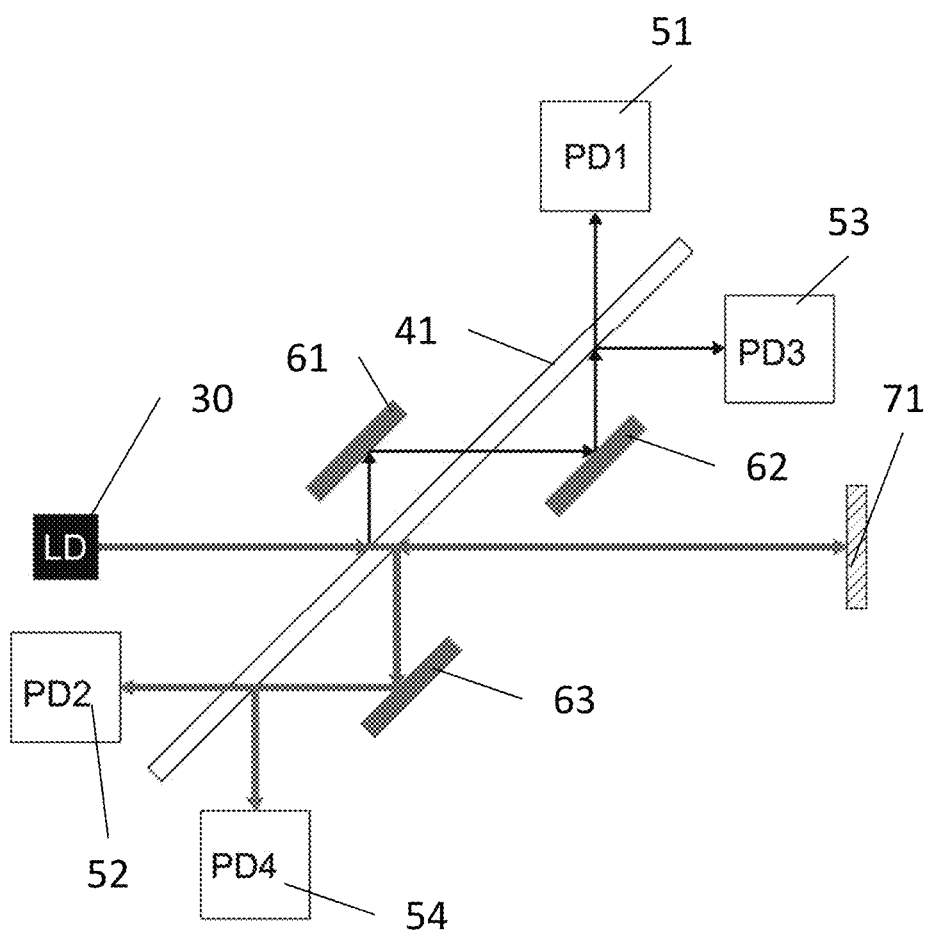
FIG. 8B shows an optical measurement device comprising a reference mirror and two pairs of photodetectors, and the calibration is confirmed with presence of a reference mirror.

In one example as illustrated in FIG. 8B, an optical measurement device comprises a light source 30, a first beam splitter 41, a first photodetector 51, a second photodetector 52, a third photodetector 53, a fourth photodetector 54, a first mirror 61, a second mirror 62, a third mirror 63 and a reference mirror 71. The reference mirror 71 may be removed after the confirmation of calibration. The light source 30 generates an emitted light beam to the first beam splitter 41. The first beam splitter 41 divides the emitted light beam into a compensation light beam and a measurement light beam. The first beam splitter 41 directs the compensation light beam to the first mirror 61 via reflection and directs the measurement light beam to an analyte 99 via transmission. The first mirror 61 reflects the compensation light beam to the first beam splitter 41. The first beam splitter 41 redirects the compensation light beam to the second mirror 62 via transmission. The second mirror 62 reflects the compensation light beam from the first beam splitter 41 back to the first beam splitter 41. The first beam splitter 41 divides the compensation light beam into a first portion of the compensation light beam and a second portion of the compensation light beam. The first beam splitter 41 redirects the first portion of the compensation light beam to the first photodetector 51 via transmission and redirects the second portion of the compensation light beam to the third photodetector 53 via reflection. The first photodetector 51 detects the first portion of the compensation light beam redirected by the first beam splitter 41 and the third photodetector 53 detects the second portion of the compensation light beam redirected by the first beam splitter 41. The first beam splitter 41 redirects the measurement light beam reflected by the analyte 99. The third mirror 63 reflects the measurement light beam from the first beam splitter 41 back to the first beam splitter 41. The first beam splitter 41 divides the measurement light beam into a first portion of the measurement light beam and a second portion of the measurement light beam. The first beam splitter 41 redirects the first portion of the measurement light beam to the second photodetector 52 via transmission and redirects the second portion of the measurement light beam to the fourth photodetector 54 via reflection. The second photodetector 52 detects the first portion of the measurement light beam redirected by the first beam splitter 41 and the fourth photodetector 54 detects the second portion of the measurement light beam redirected by the first beam splitter 41.

Figure 9A:
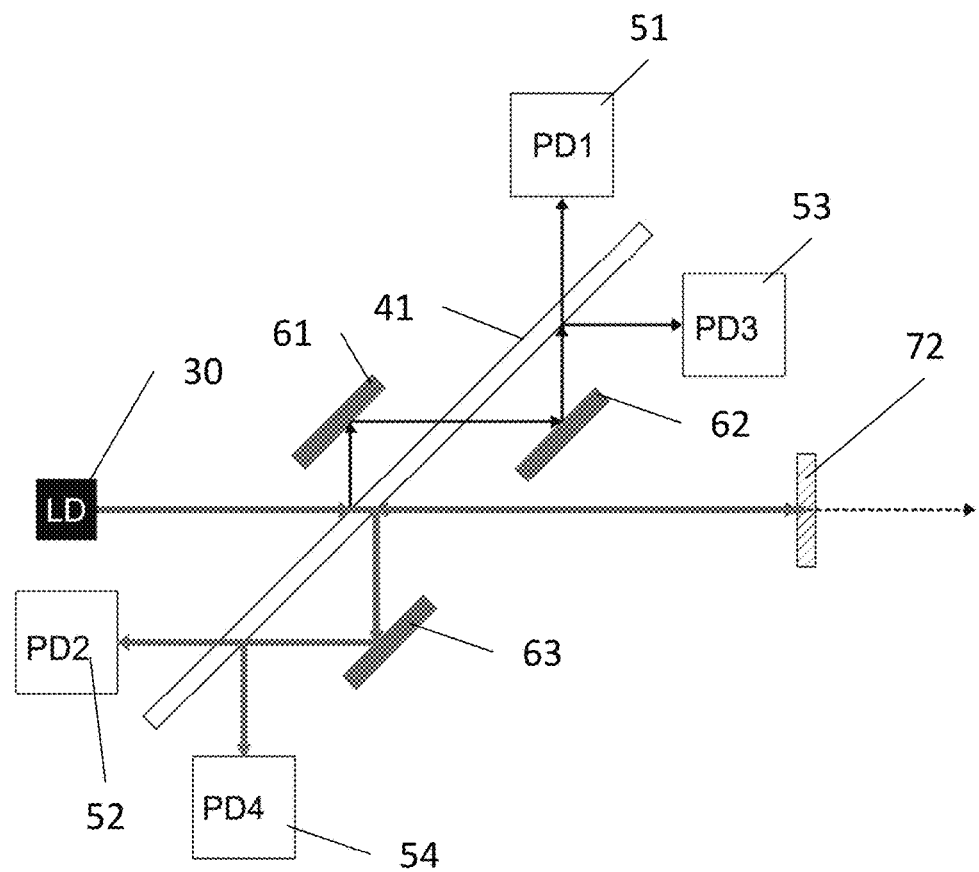
FIG. 9A shows the calibration of an optical measurement device is confirmed with presence of a partial reflective mirror.

In one example as illustrated in FIG. 9A, an optical measurement device comprises a light source 30, a first beam splitter 41, a first photodetector 51, a second photodetector 52, a third photodetector 53, a fourth photodetector 54, a first mirror 61, a second mirror 62, a third mirror 63 and a partial reflective mirror 72. The light source 30 generates an emitted light beam to the first beam splitter 41. The first beam splitter 41 divides the emitted light beam into a compensation light beam and a measurement light beam. The first beam splitter 41 directs the compensation light beam to the first mirror 61 via reflection and directs the light beam to the partial reflective mirror 72 via transmission. The first mirror 61 reflects the compensation light beam to the first beam splitter 41. The first beam splitter 41 redirects the compensation light beam to the second mirror 62 via transmission. The second mirror 62 reflects the compensation light beam from the first beam splitter 41 back to the first beam splitter 41. The first beam splitter 41 divides the compensation light beam into a first portion of the compensation light beam and a second portion of the compensation light beam. The first beam splitter 41 redirects the first portion of the compensation light beam to the first photodetector 51 via transmission and redirects the second portion of the compensation light beam to the third photodetector 53 via reflection. The first photodetector 51 detects the first portion of the compensation light beam redirected by the first beam splitter 41 and the third photodetector 53 detects the second portion of the compensation light beam redirected by the first beam splitter 41. The partial reflective mirror 72 reflects the reflected part of the measurement light beam to the first beam splitter 41 and transmits the transmitted part of the measurement light beam to the outside of the partial reflective mirror 72. The first beam splitter 41 redirects the reflected part of the measurement light beam reflected by the partial reflective mirror 72. The third mirror 63 reflects the reflected part of the measurement light beam from the first beam splitter 41 back to the first beam splitter 41. The first beam splitter 41 divides the reflected part of the measurement light beam into a first portion of the measurement light beam and a second portion of the measurement light beam. The first beam splitter 41 redirects the first portion of the measurement light beam to the second photodetector 52 via transmission and redirects the second portion of the measurement light beam to the fourth photodetector 54 via reflection. The second photodetector 52 detects the first portion of the measurement light beam redirected by the first beam splitter 41 and the fourth photodetector 54 detects the second portion of the measurement light beam redirected by the first beam splitter 41.

Figure 9B:
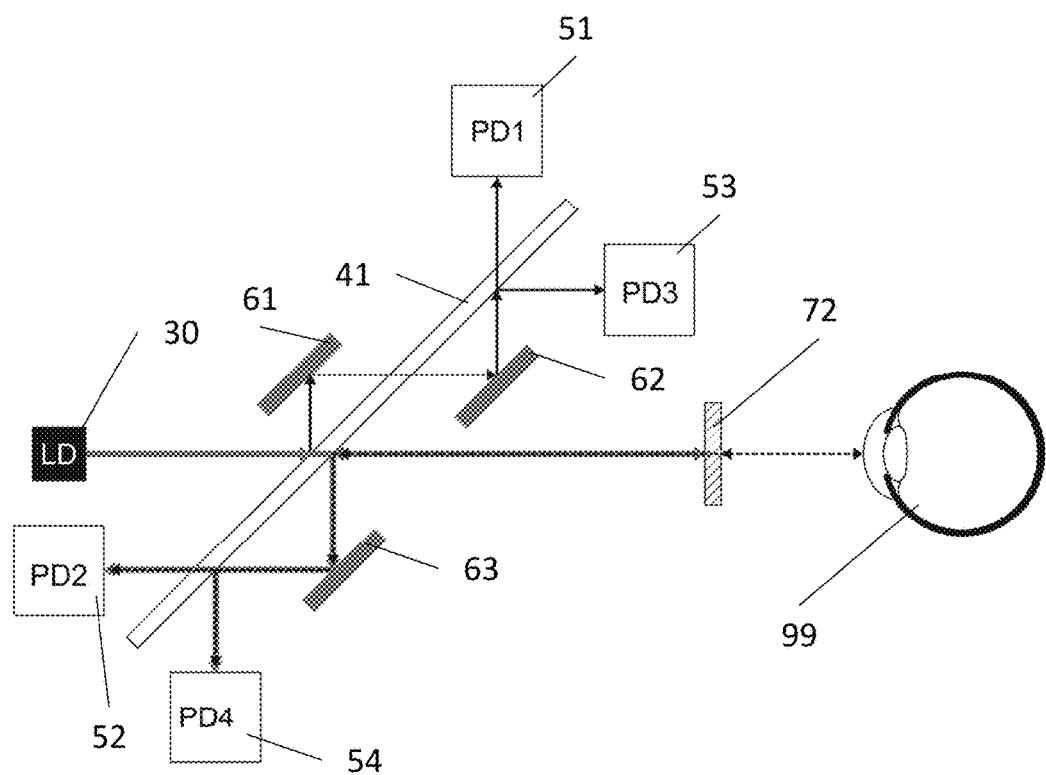
FIG. 9B shows an optical measurement device comprising a partial reflective mirror applied on an analyte.

In one example as illustrated in FIG. 9B, an optical measurement device comprises a light source 30, a first beam splitter 41, a first photodetector 51, a second photodetector 52, a third photodetector 53, a fourth photodetector 54, a first mirror 61, a second mirror 62, a third mirror 63 and a partial reflective mirror 72. The light source 30 generates an emitted light beam to the first beam splitter 41. The first beam splitter 41 divides the emitted light beam into a compensation light beam and a measurement light beam. The first beam splitter 41 directs the compensation light beam to the first mirror 61 via reflection and directs the measurement light beam to the partial reflective mirror 72 via transmission. The first mirror 61 reflects the compensation light beam to the first beam splitter 41. The first beam splitter 41 redirects the compensation light beam to the second mirror 62 via transmission. The second mirror 62 reflects the compensation light beam from the first beam splitter 41 back to the first beam splitter 41. The first beam splitter 41 divides the compensation light beam into a first portion of the compensation light beam and a second portion of the compensation light beam. The first beam splitter 41 redirects the first portion of the compensation light beam to the first photodetector 51 via transmission and redirects the second portion of the compensation light beam to the third photodetector 53 via reflection. The first photodetector 51 detects the first portion of the compensation light beam redirected by the first beam splitter 41 and the third photodetector 53 detects the second portion of the compensation light beam redirected by the first beam splitter 41. The partial reflective mirror 72 reflects the reflected part of the measurement light beam to the first beam splitter 41 and transmits the transmitted part of the measurement light beam to an analyte 99. The first beam splitter 41 redirects the measurement light beam comprising the reflected part of the measurement light beam reflected by the partial reflective mirror 72 and the transmitted part of the measurement light beam reflected by the analyte 99. The third mirror 63 reflects the measurement light beam from the first beam splitter 41 back to the first beam splitter 41. The first beam splitter 41 divides the measurement light beam into a first portion of the measurement light beam and a second portion of the measurement light beam. The first beam splitter 41 redirects the first portion of the measurement light beam to the second photodetector 52 via transmission and redirects the second portion of the measurement light beam to the fourth photodetector 54 via reflection. The second photodetector 52 detects the first portion of the measurement light beam redirected by the first beam splitter 41. The fourth photodetector 54 detects the second portion of the measurement light beam redirected by the first beam splitter 41.

Figure 10:
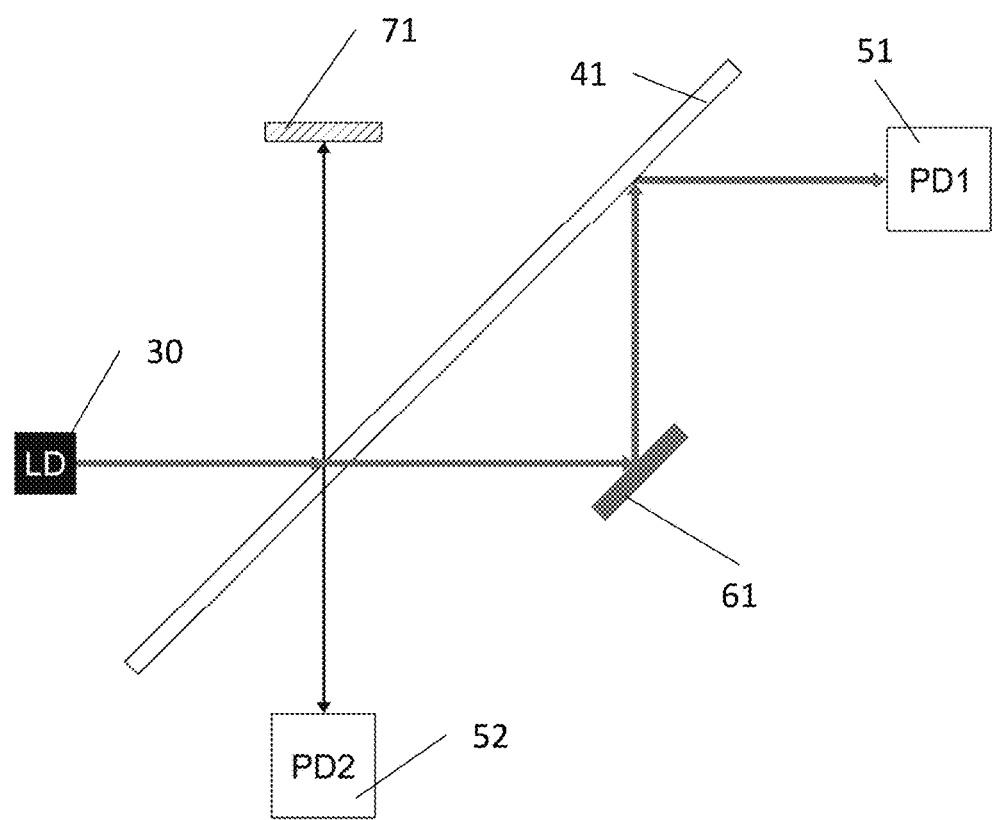
FIG. 10 shows one example of present disclosure with modified configuration.

It is contemplated that an optical measurement device may also comprise same components as all the examples mentioned above but with alternative spatial arrangements. Due to alternative arrangements, the light beams of the optical measurement device may have corresponding alternative optical path while achieving same results as the mentioned examples. As one example illustrated in FIG. 10, an optical measurement device comprises a light source 30, a first beam splitter 41, a first photodetector 51, a second photodetector 52, and a first mirror 61. The light source 30 generates an emitted light beam to the first beam splitter 41. The first beam splitter 41 divides the emitted light beam into a compensation light beam and a measurement light beam. The first beam splitter 41 directs the compensation light beam to the first mirror 61 via transmission and directs the measurement light beam to the reference mirror 71 via reflection. The first mirror 61 reflects the compensation light beam to the first beam splitter 41. The first beam splitter 41 redirects the compensation light beam to the first photodetector 51 via reflection. The first photodetector 51 detects the compensation light beam redirected by the first beam splitter 41. The first beam splitter 41 redirects the measurement light beam reflected by the reference mirror 71 via transmission. The second photodetector 52 detects the measurement light beam redirected by the first beam splitter 41.

The light power of the compensation light beam is detected by the first photodetector 51 and is denoted as $P1=P0*T1*M1*R1$. During calibration with a reference mirror 71, the measurement light beam is detected by the second photodetector 52 and is denoted as $Pr=P0*R1*Rr*T1$. The normalized power of the measurement light beam is denoted as $Pc=Pr/P1=Rr/M1$. During measurement, the reference mirror 71 is removed. Similarly, the power of the measurement light beam detected by the second photodetector 52 is denoted as $Pm=P0*R1*F*T1$. Thus, the normalized power of the measurement light beam is denoted as $Pn=Pm/P1=F/M1$. As a result, noise compensation is still achieved with the modification on the configuration of same components. It is contemplated that other examples may be compatible with the modification without departing from the scope of disclosure.

Figure 11:
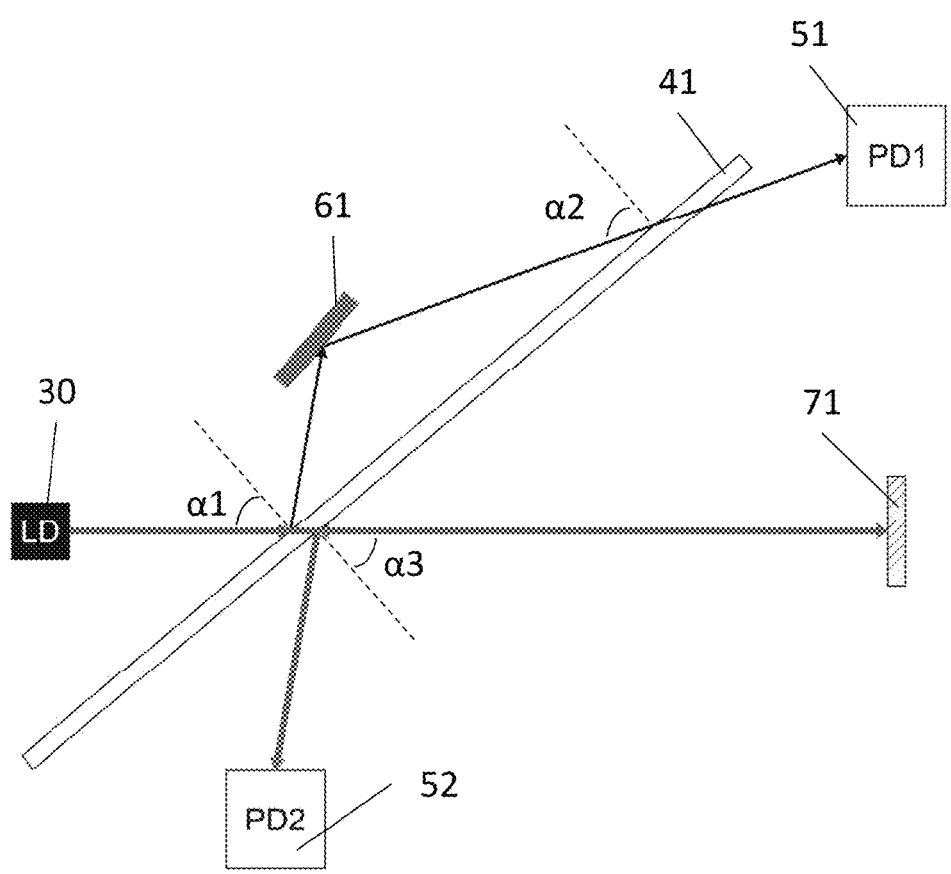
FIG. 11 shows one example comprising components configured with various degrees of angle.

The present disclosure may have different configurations with various incident angles. The transmittance-wavelength characteristic curve may be dependent on the incident angle. However, the variation may be tolerable in most cases. The incident angle, $\alpha$, is defined as an angle between a light beam (for example, compensation light beam or measurement light beam) and the line perpendicular to the beam splitter at the point of incidence. Although all the examples mentioned above are embodied with an incident angle of 45 degree, it is contemplated that the incident angle may varies from zero to ninety degree (zero and ninety degree not included). Furthermore, the incident angles may not be exactly the same in some examples. In one example in FIG. 11, the incident angle $\alpha 1$ and $\alpha 3$ are inherently the same, while $\alpha 1$ and $\alpha 2$ may be different as long as the transmittance at $\alpha 1$ is about the same as the transmittance at $\alpha 2$. Specifically, the normalized power of the measurement light beam is denoted as $Pc=Pr/P1=P0*T\alpha 1*Rr*R\alpha 3/P0*R\alpha 1*M1*T\alpha 2$, where $T\alpha 1$ is the transmittance at $\alpha 1$, $R\alpha 3$ is the reflectance at $\alpha 3$, $R\alpha 1$ is the reflectance at $\alpha 1$, and $T\alpha 2$ is the transmittance at $\alpha 2$. Obviously, $Pc=Rr*T\alpha 1/M1*T\alpha 2$ when $\alpha 1=\alpha 3$, and noise compensation is still achieved if $T\alpha 1$ and $T\alpha 2$ are around the same or proportional around a certain range of wavelength of the emitted light. Similarly, all the examples mentioned above may also have various adjustment of incident angles under the framework of present disclosure.

Figure 12:
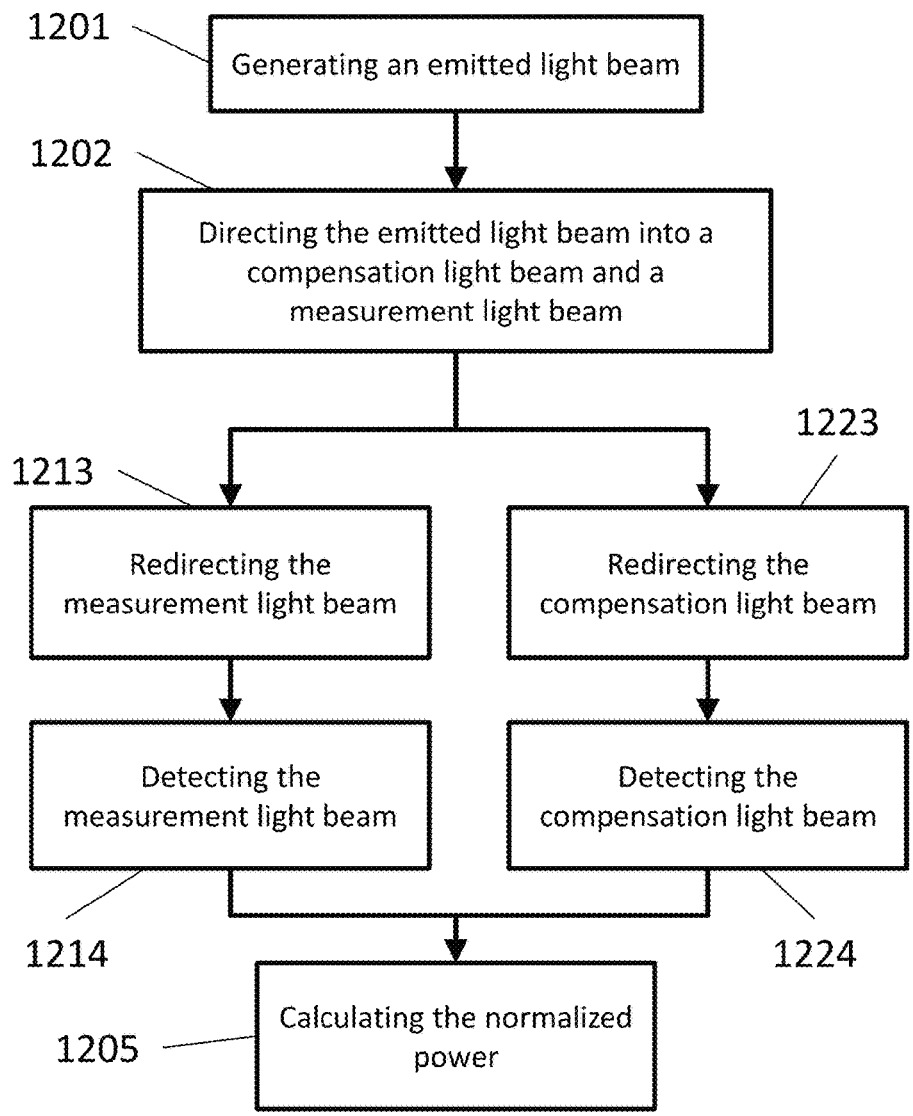
FIG. 12 shows a flow diagram of the method for optical measurement.

In FIG. 12, the flow diagram shows an optical measurement method. The optical measurement method comprising the steps: generating an emitted light beam 1201; directing the emitted light beam and a measurement light beam 1202; redirecting the measurement light beam 1213; redirecting the compensation light beam 1223; detecting the measurement light beam 1214; detecting the compensation light beam 1224; and calculating the normalized power 1205. The step 1201 is accomplished by a light source. The step 1202 is accomplished by a beam splitter, wherein a beam splitter may be a first beam splitter. The step 1213 and the step 1223 is accomplished by the beam splitter. The step 1214 is accomplished by a first photodetector and the step 1214 is accomplished by a second photodetector. The step 1205 is accomplished by a microprocessor. In the example of the beam splitter comprising a first beam splitter and the second beam splitter. The step 1202 is accomplished by the first beam splitter. The step 1213 is accomplished by the first beam splitter and the step 1223 is accomplished by the second beam splitter.

The examples shown and described above are only examples. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including the full extent established by the broad general meaning of the terms used in the claims. It will therefore be appreciated that the examples described above may be modified within the scope of the claims.

What is claimed is:

1. An optical measurement device comprising:
    a light source that generates an emitted light beam;
    a first beam splitter that divides the emitted light beam into a compensation light beam and a measurement light beam, wherein the first beam splitter directs the measurement light beam to a target via transmission or reflection;
    a second beam splitter that redirects the compensation light beam from the first beam splitter via transmission or reflection, wherein a part of wavelength dependent characteristics of the first beam splitter and the second beam splitter are the same;
    a first photodetector that detects the compensation light beam redirected from the second beam splitter; and
    a second photodetector that detects the measurement light beam reflected by the target and redirected by the first beam splitter, wherein a first optical path couples the light source and the first photodetector, the compensation light beam is subjected to at least one transmission and at least one reflection along the first optical path, a second optical path couples the light source and the second photodetector, the measurement light beam is subjected to at least one transmission and at least one reflection along the second optical path, an amount of transmission by the first beam splitter or the second beam splitter in the first optical path is equal to an amount of transmission by the first beam splitter in the second optical path, and an amount of reflection by the first beam splitter or the second beam splitter in the first optical path is equal to an amount of reflection by the first beam splitter in the second optical path.

2. The optical measurement device according to claim 1, wherein
the first beam splitter directs the measurement light beam to the target via transmission; and
the second beam splitter redirects the compensation light beam reflected from the first beam splitter via transmission.

3. The optical measurement device according to claim 1, wherein
the first beam splitter directs the measurement light beam to the target via reflection; and
the second beam splitter redirects the compensation light beam transmitted from the first beam splitter via reflection.

4. The optical measurement device according to claim 1, wherein the target is a reference mirror that reflects the measurement light beam to the first beam splitter.

5. The optical measurement device according to claim 1, further comprising a partial reflective mirror that transmits a transmitted part of the measurement light beam to the target and reflects a reflected part of the measurement light beam to the first beam splitter.

6. The optical measurement device according to claim 1, wherein the light source is a coherent light source.

7. The optical measurement device according to claim 1, further comprising a first mirror that reflects the compensation light beam from the first beam splitter to the first beam splitter.

8. An optical measurement device comprising:
a light source that generates an emitted light beam;
a first beam splitter that divides the emitted light beam into a compensation light beam and a measurement light beam;
a first mirror that reflects the compensation light beam from the first beam splitter to the first beam splitter;
a second mirror reflects the compensation light beam from the first mirror via the first beam splitter to the first beam splitter;
a third mirror reflects the measurement light beam from the first beam splitter to the first beam splitter;
a first photodetector that detects a first portion of the compensation light beam redirected by the first beam splitter;
a second photodetector that detects a first portion of the measurement light beam redirected by the first beam splitter;
a third photodetector detects a second portion of the compensation light beam; and
a fourth photodetector detects a second portion of the measurement light beam.

9. The optical measurement device according to claim 8, wherein the target is a reference mirror that reflects the measurement light beam to the first beam splitter.

10. The optical measurement device according to claim 8, further comprising:
a partial reflective mirror that transmits a transmitted part of the measurement light beam to the target and reflects a reflected part of the measurement light beam to the first beam splitter.

11. The optical device according to claim 8, wherein the light source is a coherent light source.

12. The optical device according to claim 8, wherein a part of wavelength dependent characteristics of the first beam splitter and the second beam splitter are the same.

13. An optical measurement method comprising:
generating an emitted light beam by a light source;
directing the emitted light beam into a compensation light beam and a measurement light beam by a beam splitter;
redirecting the compensation light beam into a first portion of the compensation light beam and a second portion of the compensation light beam by the beam splitter;
redirecting the measurement light beam into a first portion of the measurement light beam and a second portion of the measurement light beam by the beam splitter;
detecting the first portion of the compensation light beam by a first photodetector and detecting the second portion of the compensation light beam by a third photodetector; and
detecting the first portion of the measurement light beam by the second photodetector; and
detecting the second portion of the compensation light beam by a fourth photodetector.

14. The optical measurement method according to claim 13, further comprising:
reflecting the measurement light beam by a reference mirror before the step for redirecting the measurement light beam.

15. The optical measurement method according to claim 13, further comprising:
reflecting a reflected part of the measurement light beam and transmitting a transmitted part of the measurement light beam by a partial reflective mirror before the step for redirecting the measurement light beam.

16. The optical measurement method according to claim 13, wherein
the beam splitter comprises a first beam splitter and a second beam splitter,
the step for directing the emitted light beam is accomplished by the first beam splitter,
the step for redirecting the compensation light beam is accomplished by the second beam splitter, and
the step for redirecting the measurement light beam is accomplished by the first beam splitter.

* * * * *